United States Patent
Lindsell et al.

(10) Patent No.: US 10,815,526 B2
(45) Date of Patent: Oct. 27, 2020

(54) TEMPORAL PEDIATRIC SEPSIS BIOMARKER RISK MODEL

(71) Applicants: CHILDREN'S HOSPITAL MEDICAL CENTER, Cincinnati, OH (US); Christopher John Lindsell, Cincinnati, OH (US)

(72) Inventors: Christopher John Lindsell, Cincinnati, OH (US); Hector R. Wong, Cincinnati, OH (US)

(73) Assignees: CHILDREN'S HOSPITAL MEDICAL CENTER, Cincinnati, OH (US); UNIVERSITY OF CINCINNATI, Cincinnati, OH (US)

( * ) Notice: Subject to any disclaimer, the term of this patent is extended or adjusted under 35 U.S.C. 154(b) by 1028 days.

(21) Appl. No.: 15/038,862

(22) PCT Filed: Nov. 25, 2014

(86) PCT No.: PCT/US2014/067438
§ 371 (c)(1),
(2) Date: May 24, 2016

(87) PCT Pub. No.: WO2015/077781
PCT Pub. Date: May 28, 2015

(65) Prior Publication Data
US 2016/0376654 A1 Dec. 29, 2016

Related U.S. Application Data (60) Provisional application No. 61/908,613, filed on Nov. 25, 2013.

(51) Int. Cl.
*G01N 31/00* (2006.01)
*G01N 33/53* (2006.01)
*C12Q 1/6883* (2018.01)

(52) U.S. Cl.
CPC ..... *C12Q 1/6883* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,645,573 B2 | 1/2010 | Ivey et al. | |
| 8,969,017 B2 | 3/2015 | Mickiewicz | |
| 9,238,841 B2 * | 1/2016 | Wong | C12Q 1/6883 |
| 9,267,175 B2 | 2/2016 | Wong et al. | |
| 10,078,086 B2 | 9/2018 | Wong | |
| 10,261,068 B2 | 4/2019 | Wong | |
| 2003/0194752 A1 | 10/2003 | Anderson et al. | |
| 2004/0121343 A1 | 6/2004 | Buechler et al. | |
| 2009/0297474 A1 | 12/2009 | Kelleher | |
| 2010/0004253 A1 | 1/2010 | Aziz et al. | |
| 2010/0279878 A1 | 11/2010 | Wong | |
| 2011/0059858 A1 | 3/2011 | Kas et al. | |
| 2011/0312521 A1 | 12/2011 | Chaussabel | |
| 2012/0094315 A1 | 4/2012 | Fryar-Williams | |
| 2015/0005189 A1 | 1/2015 | Wong et al. | |
| 2015/0018238 A1 | 1/2015 | Wong et al. | |
| 2015/0233942 A1 | 8/2015 | Wong | |
| 2016/0356762 A1 | 12/2016 | Wong | |

FOREIGN PATENT DOCUMENTS

| | | |
|---|---|---|
| EP | 2085486 A1 | 8/2009 |
| WO | WO-2004/044554 A2 | 5/2004 |
| WO | WO-2004/044554 A3 | 5/2004 |
| WO | WO-2006/113529 A2 | 10/2006 |
| WO | WO-2006/113529 A3 | 10/2006 |
| WO | WO-2006/113833 A2 | 10/2006 |
| WO | WO-2006/113833 A3 | 10/2006 |
| WO | 2007100631 A2 | 9/2007 |
| WO | WO-2008/143890 A2 | 11/2008 |
| WO | WO-2008/143890 A3 | 11/2008 |
| WO | WO-2009/095786 A2 | 8/2009 |
| WO | WO-2009/095786 A3 | 8/2009 |
| WO | WO-2009/095840 A1 | 8/2009 |
| WO | WO-2009/123737 A2 | 10/2009 |
| WO | WO-2009/123737 A3 | 10/2009 |
| WO | WO-2010/049818 A1 | 5/2010 |

(Continued)

OTHER PUBLICATIONS

Wong et al. Critical Care 2012, vol. 16, R174, pp. 1-9).*
Verboon-Maciolek et al. (Pediatric Research, Vo.59, No. 3, 2006).*
Standage and Wong (Expert Rev. Anti. Infect. Ther, Jan. 2011, 9(1) pp. 71-79).*
Kaplan et. al. (Pediatric Critical Care Medicine, Mar. 2011, 12(2), pp. 165-173).*
Wong etal. Critical Care 2012, vol. 16, R174, pp. 1-9). (Year: 2012).*
Verboon-Macioleketal. (Pediatric Research, Vo.59, No. 3, 2006) (Year: 2006).*
Standage and Wong (Expert Rev. Anti. Infect. Ther, Jan. 2011, 9(1) pp. 71-79). (Year: 2011).*

(Continued)

*Primary Examiner* — Lisa V Cook
(74) *Attorney, Agent, or Firm* — Muriel Liberto, Esq.; Mintz Levin Cohn Ferris Glovsky and Popeo, P.C.

(57) ABSTRACT

Methods and compositions disclosed herein generally relate to methods of identifying, validating, and measuring clinically relevant, quantifiable biomarkers of diagnostic and therapeutic responses for blood, vascular, cardiac, and respiratory tract dysfunction, particularly as those responses relate to septic shock in pediatric patients. In particular, the invention relates to identifying one or more biomarkers associated with septic shock in pediatric patients, obtaining a sample from a pediatric patient having at least one indication of septic shock, then quantifying from the sample an amount of one or more of said biomarkers, wherein the level of said biomarker correlates with a predicted outcome.

10 Claims, 2 Drawing Sheets

(56) References Cited

FOREIGN PATENT DOCUMENTS

| WO | WO-2012/106396 A2 | 8/2012 |
|---|---|---|
| WO | WO-2012/106396 A9 | 8/2012 |
| WO | WO-2013/119869 A1 | 8/2013 |
| WO | WO-2013/119871 A1 | 8/2013 |
| WO | WO-2014/036518 A2 | 3/2014 |
| WO | 2015077781 A1 | 5/2015 |

OTHER PUBLICATIONS

Kaplan et. al. (Pediatric Critical Care Medicine, Mar. 2011, 12(2), pp. 165-173). (Year: 2011).*
Wong et al. "Validation of a gene expression-based subclassification strategy for pediatric septic shock," Crit Care Med. Nov. 1, 2011 (Nov. 1, 2011) vol. 39, pp. 1-18.
Standage et al. "Biomarkers for pediatric sepsis and septic shock," Expert Rev Anti Infect Ther. Jan. 1, 2011 (Jan. 1, 2011), vol. 9, pp. 1-15.
International Search Report issued in PCT/US2014/067438 dated Feb. 20, 2015.
Abulebda , A. et al. (Oct. 18, 2013). "Post-intensive care unit admission fluid balance and pediatric septic shock outcomes: A risk-stratified analysis," *Crit. Care Med.* 42(2):397-403.
Alder et al., "The pediatric sepsis biomarker risk model: potential implications for sepsis therapy and biology," Expet Rev. Anti Infect. Ther., 2014, pp. 809-816, vol. 12(7).
Allen, T.C. et al. (Mar. 2007). "Anti-interleukin 8 autoantibody:interleukin 8 immune complexes visualized by laser confocal microscopy in injured lung," *Arch Pathol Lab Med* 131(3):452-456.
Allison et al., "Microarray data analysis: from disarray to consolidation and consensus," Nat. Rev. Genet., Jan. 2006, pp. 55-65, vol. 7(1) [abstract only].
Aneja, R.K. et al. (Oct. 2011). "Differences Between Adult and Pediatric Septic Shock," *Minerva Anestesiologica* 77(10): 986-992.
Brierley et al., "Clinical practice parameters for hemodynamic support of pediatric and neonatal septic shock: 2007 update from the American College of Critical Care Medicine," Crit. Care Med., 2009, pp. 666-688, vol. 37(2).
Brunkhorst, F.M. et al. (Mar. 2002). "Diagnostic approach to sepsis—state of the art," *Zentralbl Chir* 127(3):165-173 (Translation of Abstract only).
Che, D. et al. (2011). "Decision tree and ensemble learning algorithms with their applications in bioinformatics," *Adv. Exp. Med. Biol.*, 696:191-199.
Czaja et al., "Readmission and late mortality after pediatric severe sepsis," Pediatrics, Mar. 2009, pp. 849-857, vol. 123(3) [abstract only].
Cornell et al., "Mechanisms and regulation of the gene-expression response to sepsis," Pediatrics., Jun. 2010, pp. 1248-1258, vol. 125(6).
Cvijanovich et al., "Validating the genomic signature of pediatric septic shock," Physiol. Genomics., Jun. 12, 2008, pp. 127-134, vol. 34(1).
Dellinger et al., "Surviving Sepsis Campaign: international guidelines for management of severe sepsis and septic shock: 2008," A26.
Dellinger, R.P. et al. (Feb. 2013). "Surviving sepsis campaign: international guidelines for management of severe sepsis and septic shock: 2012," *Crit. Care Med.* 41(2):580-637.
Dombrovskiy et al., "Rapid increase in hospitalization and mortality rates for severe sepsis in the United States: a trend analysis from 1993 to 2003," Crit. Care Med., May 2007, pp. 1244-1250, vol. 35(5).
Freishtat et al., "Sepsis Alters the Megakaryocyte-Platelet Transcriptional Axis Resulting in Granzyme B-mediated Lymphotoxicity," Am. J. Respir. Crit. Care Med., 2009, pp. 467-473, vol. 179.
Hanley et al., "A method of comparing the areas under receiver operating characteristic curves derived from the same cases," Radiology, Sep. 1983, pp. 839-843, vol. 148(3).

Kaplan et al., "Changes in peroxisome proliferator activated receptor-gamma activity in children with septic shock," Intensive Care Med., Jan. 2010, pp. 123-130, vol. 36(1).
Kaplan, J.M. et al. (Mar. 2011). "Biomarker discovery and development in pediatric critical care medicine," *Pediatric Crit Care Med* 12(2):165-173.
Kartal, E.D. et al. (Jun. 2012, e-published Jun. 1, 2012). "Several Cytokines and Protein C Levels with the Apache II Scoring System for Evaluation of Patients with Sepsis," *Balkan Medical Journal* 29(2): 174-178.
Hack, E. et al. (Jul. 1992). "Interleukin-8 in relation to shock and inflammatory mediators", *Infection and Immunity, American Society for Microbiology*: 60(7): 2835-2842.
Hanley, J.A. et al. (Sep. 1983). "A method of comparing the areas under receiver operating characteristic curves derived from the same cases," *Radiology* 148(3): 839-843.
Hein, O.V. et al. (2005). "Time course of endothelial damage in septic prediction of outcome," *Critical Care, Biomed Central Ltd.* 9(4): R307-R314.
Giuliano et al., "Admission Angiopoietin Levels in Children with Septic Shock," Shock, Dec. 2007, pp. 650-654, vol. 28(6).
Goldstein et al. "International Pediatric Sepsis Consensus Conference: Definitions for Sepsis and Organ Dysfunction in Pediatrics," Pediatric Crit Care Med Jan. 2005 pp. 2-8, vol. 6(1) [abstract only].
Livaditi, O. et al. (Dec. 2006, e-published Mar. 26, 2007). "Neutrophil CD64 expression and serum IL-8: sensitive early markers of severity and outcome in sepsis," Cytokine 36(5-6):283-290.
Levy, M.M. et al. (Feb. 2010). "The Surviving Sepsis Campaign: results of an international guideline-based performance improvement program targeting severe sepsis," *Crit. Care Med.* 38(2): 367-374.
Lokshin, A.E. et al. (Aug. 2006, e-published Jan. 24, 2006). "Circulating IL-8 and anti-IL-8 autoantibody in patients with ovarian cancer," *Gynecol Oncol* 12(2):244-251.
Marshall, "Sepsis: rethinking the approach to clinical research," J. Leukoc. Biol., Mar. 2008, 471-482, vol. 83(3).
Marshall et al., "Biomarkers of sepsis," Crit. Care Med., Jul. 2009, pp. 2290-2298, vol. 37(7) [abstract only].
Maslove et al., "Gene expression profiling in sepsis: timing, tissue, and translational considerations," Trends in Molecular Medicine, Apr. 2014, pp. 204-213, vol. 20(4).
Mera, S. et al. (Feb. 2011, e-published Dec. 10, 2010). "Multiplex cytokine profiling in patients with sepsis," *APMIS* 119(2):155-163.
Mickiewicz B. et al. (2013). "Metabolomics as a Novel Approach for Early Diagnosis of Pediatric Septic Shock and Its Mortality," *Am. J. Respir. Crit. Care Med.* 187:967-976.
Muller et al., "Logistic regression and CART in the analysis of multimarker studies," Clin. Chim. Acta., Aug. 2008, pp. 1-6, vol. 394(1-2).
Nadel et al. Drotrecogin alfa (activated) in children with severe sepsis: a multicenter phase III randomized controlled trial, Lancet, Mar. 10, 2007, pp. 836-843, vol. 369(564)—abstract only.
Nichol, A.D. et al. (2010). "Relative hyperlactatemia and hospital mortality in critically ill patients: a retrospective multi-centre study," *Crit. Care.* 14:R25, 9 pages.
Nowak et al., Admission Chemokine (C-C motif) Ligand 4 Levels Predict Survival in Pediatric Septic Shock, Pediatr. Crit. Care Med., Mar. 2010, pp. 213-216, vol. 11(2).
Osuchowski et al., "Stratification is the key: inflammatory biomarkers accurately direct immunomodulatory therapy in experimental sepsis," Crit. Care Med., May 2009, pp. 1567-1573, vol. 37(5).
Patent Cooperation Treaty, "International Preliminary Report on Patentability and Written Opinion" in corresponding International application No. PCT/US2013/025223, dated Aug. 12, 2014, 5 pgs.
Patent Cooperation Treaty, "International Search Report" in corresponding International application No. PCT/US2013/025223, dated May 30, 2013, 2 pgs.
Pollack et al., "The Pediatric Risk of Mortality III-Acute Physiology Score (PRISM III-APS): a method of assessing physiologic instability for pediatric intensive care unit patients," J Pediatr., Oct. 1997, pp. 575-581, vol. 131(4) [abstract only].
Ranieri, V.M. et al., (May 31, 2012)."Drotrecogin alfa (activated) in adults with septic shock," *N. Engl. J. Med.* 366(22):2055-2064.

(56) References Cited

OTHER PUBLICATIONS

Russell, J.A. et al. (Feb. 28, 2008). "Vasopressin versus norepinephrine infusion in patients with septic shock," *N. Engl. J. Med.* 358(9):877-887.
Shanley et al., "Genome-Level Longitudinal Expression of Signaling Pathways and Gene Networks in Pediatric Septic Shock," MOL MED, Sep.-Oct. 2007, pp. 495-508, vol. 13(9-10).
Sharron et al., "Platelets Induce Apoptosis during Sepsis in a Contact-Dependent Manner That Is Inhibited by GPIIb/IIIa Blockade," PLoS ONE, Jul. 2012, p. e41549, vol. 7(7).
Solan et al., "A novel role for matrix metalloproteinase-8 in sepsis," Crit Care Med., Feb. 2012, pp. 379-387, vol. 40(2).
Standage et al., Biomarkers for pediatric sepsis and septic shock, Expert Rev. Anti Infect. Ther., 2011, pp. 71-79.
Sweeney et al., "Recombinant human activated protein C, package labeling, and hemorrhage risks," Crit. Care Med., Jan. 2009, pp. 327-329, vol. 37(1).
Verboon-Maciolek, M.A. et al. (Mar. 2006). "Inflammatory mediators for the diagnosis and treatment of sepsis in early infancy," *Pediatr Res* 59(3):457-461.
Vermont Clementien L et al:CC and CXC chemokine levels in children with meningococcal sepsis accurately mortality and disease severity, Critical Care, Biomed Central Ltd., 10(1):1-8 (2006).
Vincent, et al., "Ten reasons why we should NOT use severity scores as entry criteria for clinical trials or in our treatment decisions," Crit Care Med., Jan. 2010, pp. 283-287, vol. 38(1) [abstract only].
Wacharasint, P. et al. (Jul. 2012). "Normal-range blood lactate concentration in septic shock is prognostic and predictive," *Shock* 38(1):4-10.
Watson et al., "Scope and epidemiology of pediatric sepsis," Pediatr Crit Care Med, 2005, vol. 6(3), (Suppl.).
Watson et al., "The Epidemiology of Severe Sepsis in Children in the United States," Am J Respir Crit Care Med, 2003, pp. 695-701, vol. 167.
Wheeler et al., "Extracellular heat shock protein 60 (Hsp60) levels in children with septic shock," Inflamm Res., May 2007, pp. 216-219, vol. 56(5) [abstract only].
Wheeler et al., "Extracellular hsp70 levels in children with septic shock," Pediatr Crit Care Med. May 2005, pp. 308-311 vol. 6(3) [abstract only].
Wheeler et al., "Serum Neutrophil Gelatinase-associated Lipocalin (NGAL) as a Marker of Acute Kidney Injury in Critically Ill Children with Septic Shock," Crit Care Med., Apr. 2008, pp. 1297-1303, vol. 36(4).
Wong et al., "Increased serum nitrite and nitrate concentrations in children with the sepsis syndrome," Crit Care Med., May 1995, pp. 835-842, vol. 23(5) [abstract only].
Wong et al., "Plasma bactericidal/permeability-increasing protein concentrations in critically ill children with the sepsis syndrome," Pediatr Infect Dis J., Dec. 1995, pp. 1087-1091, vol. 14(12) [abstract only].
Wong et al., "Genome-level expression profiles in pediatric septic shock indicate a role for altered zinc homeostasis in poor outcome," Physiol. Genomics., Jul. 18, 2007, pp. 146-155, vol. 30(2).
Wong, "Pediatric septic shock treatment: new clues from genomic profiling," Pharmacogenetics, Oct. 2007, pp. 1287-1290, vol. 8(10).
Wong et al., "Genomic expression profiling across the pediatric systemic inflammatory response syndrome, sepsis, and septic shock spectrum," Crit. Care Med., May 2009, pp. 1558-1566, vol. 37(5).
Wong, H.R. et al. "The pediatric sepsis biomarker risk model", Critical Care, Biomed Central Ltd., 16(5):1-9 (2012).
Wong et al., "Testing the Prognostic Accuracy of the Updated Pediatric Sepsis Biomarker Risk Model," PLoS ONE, Jan. 2014, pp. e86242 (6 pgs.), vol. 9(1).
Wong et al., "The Temporal Version of the Pediatric Sepsis Biomarker Risk Model," PLoS ONE, Mar. 2014, pp. e92121 (7 pgs.), vol. 9(3).
Wong et al., "A Multibiomarker-Based Outcome Risk Stratification Model for Adult Septic Shock," Critical Care Medicine, Apr. 2014, pp. 781-789, vol. 42(4).

Wynn, J. et al. (May 2010). "The host response to sepsis and developmental impact," *Pediatrics* 125(5):1031-1041.
Basu et al. (2011). "Identification of Candidate Serum Biomarkers for Severe Septic Shock-Associated Kidney Injury via Microarray." *Crit. Care.* 15.6(2011):R273.
Eichler et al. (2002). "Gene Expression Dynamics Inspector (GEDI): For Integrative Analysis of Expression Profiles." *Bioinformatics.* 19.17:2321-2322.
Guo et al. (2006). "Towards a Holistic, yet Gene-Centered Analysis of Gene Expression Profiles: A Case Study of Human Lung Cancers." *J. Biomed. Biotechnol.* 2006.5:69141.
Irizarry et al. (2003). "Exploration, Normalization, and Summaries of High Density Oligonucleotide Array Probe Level Data." *Biostatistics.* 4.2:249-264.
Lee et al. "(2003). Classification of Multiple Cancer Types by Multicategory Support Vector Machines Using Gene Expression Data." *Bioinformatics.* 19.9:1132-1139.
Pflanz et al. (2002). "IL-27, a Heterodimeric Cytokine Composed of EB13 and p28 Protein, Induces Proliferation of Naïve CD4+ T Cells." *Immunity.* 16.6:779-790.
Sutherland et al. (2011). "Development and Validation of a Novel Molecular Biomarker Diagnostic Test for the Early Detection of Sepsis." *Crit. Care.* 15.3:R149.
Tang et al. (2007). "Accuracy of Procalcitonin for Sepsis Diagnosis in Critically Ill Patients: Systematic Review and Meta-Analysis." *Lancet Infect. Dis.* 7.3:210-217.
Tang et al. (2007). "The Use of Gene-Expression Profiling to Identify Candiate Genes in Human Sepsis." *Am. J. Respir. Crit. Care Med.* 176.7:676-684.
Villarino et al. (2005). "Positive and Negative Regulation of the IL-27 Receptor During Lymphoid Cell Activation." *J. Immunol.* 174.12:7684-7691.
Wirtz et al. (2006). "Protection from Lethal Septic Peritonitis by Neutralizing the Biological Function of Interleukin 27." *J. Exp. Med.* 203.8:1875-1881.
Wojno et al. (2012). "New Directions in the Basic and Translational Biology of Interleukin-27." *Trends Immunol.* 33.2:91-97.
Wong et al. (2009). "Genomic Expression Profiling Across the Pediatric Systemic Inflammatory Response Syndrome, Sepsis, and Septic Shock Spectrum." *Crit. Care Med.* 37.5:1558-1566.
Wong et al. (2009). "Identification of Pediatric Septic Shock Subclasses Based on Genome-Wide Expression Profiling." *BMC Med.* 7:34.
Wong et al. (2008). "Interleukin-8 as Stratification Tool for Interventional Trials Involving Pediatric Septic Shock." *Am. J. Respir. Crit. Care Med.* 178.3:276-282.
Wong et al. (2010). "Leukocyte Subset-Derived Genomewide Expression Profiles in Pediatric Septic Shock." *Pediatr. Crit. Care Med.* 11.3:349-355.
Wong et al. (2010). "Toward a Clinically Feasible Gene Expression-Based Subclassification Strategy for Septic Shock: Proof of Concept." *Crit. Care Med.* 38.10:1955-1961.
Wong, H. (2012). "Clinical Review: Sepsis and Septic Shock—The Potential of Gene Arrays." *Crit. Care.* 16.1:204.
Wong, H. (2012). "Genetics and Genomics in Pediatric Septic Shock." *Crit. Care Med.* 40.5:1618-1620.
Wynn et al. (2011). "The Influence of Developmental Age on the Early Transcriptomic Response of Children with Septic Shock." *Mol. Med.* 17:1146-1156.
Cunha, B. (2008). "Sepsis and septic shock: selection of empiric antimicrobial therapy." *Crit. Care Clinics* 24(2):313-334.
Xu et al. (2013). "IL-27 is elevated in acute lung injury and mediates inflammation." *J. Clin. Immunol.* 33:1257-1268.
Wong et al. (2012). "Interleukin-27 is a novel candidate diagnostic biomarker for bacterial infection in critically ill children." *Critical Care* ccforum.com/content/16/5/R213, pp. 1-8.
Mokert et al. (2005). "Procalcitonin, interleukin 6 and systemic inflammatory response syndrome (SIRS): early markers of postoperative sepsis after major surgery." *Brit. J. Anaesthesia* 94(6):767-773.
Morgan et al. (2004). "Cytometric bead array: a multiplexed assay platform with applications in various areas of biology." *Clin. Immunol.* 110:252-266.

(56) References Cited

OTHER PUBLICATIONS

Yoshizaki et al. (2011). "Elevated serum interleukin-27 levels in patients with systemic sclerosis: association with T cell, B cell and fibroblast activation." *Ann. Rheum. Disease* 70:194-200.

Hartmann et al. (2009). "Protein microarrays for diagnostic assays." *Anal. Bioanal. Chem.* 393:1407-1416.

Simon et al. (2004). "Serum procalcitonin and C-reactive protein levels as markers of bacterial infection: A systematic review and meta-analysis." *Clin. Inf. Diseases* 39:206-217.

Jafarzadeh et al. (2011). "Serum levels of interleukin (IL)-17 in patients with ischemic heart disease." *Cytokine* 56:153-156.

Dellinger et al. (2013). Surviving sepsiscampaign: internaltional guidelines for management of severe sepsis and septic shock, 2012. *Intensive Care Med.* 39:165-228.

Knox et al. (May 2015, e-published Apr. 8, 2015). "Phenotypic clusters within sepsis-associated multiple organ dysfunction syndrome," *Intensive Care Med* 41(5):814-822.

Hanna et al. (Apr. 2013, e-published Jan. 3, 2013). "Pediatric sepsis: challenges and adjunctive therapies," *Crit Care Clin* 29(2):203-222.

Temple, R. et al. (Dec. 2010, e-published Oct. 13, 2010). "Enrichment of clinical study populations," *Clin Pharmacol Ther* 88(6):774-778.

Chen et al. (2016). "Predictors of in-hospital mortality for sepsis patients in intensive care units." *Int. J. Clin. Exp. Med.* 9(2):4029-4034.

Guclu et al. (2013). "Effect of severe sepsis on platelet count and their indices." *Afr. Health. Scis.* 13(2):333-338.

Steyerberg et al. (Jan. 2010). "Assessing the performance of prediction models: a framework for traditional and novel measures," *Epidemiology* 21(1):128-138.

Venkata et al. (2013). "Thrombocytopenia in adult patients with sepsis: incidence, risk factors, and its association with clinical outcome." *J. Inten. Care* 1(9):1-10.

Boechat et al. (2012). "Thrombocytopenia in sepsis: an important prognosis factor." *Rev. Bras. Ter. Intensiva.* 24(1):35-42.

Spies et al. (2003). "Prediction of mortality from catastrophic burns in children." *Lancet* 361:989-994.

Nyugen et al. (2006). "Bench-to-bedside review: thrombocytopenia-associated multiple organ failure—a newly appreciated syndrome in the critically ill." *Crit. Care* 10(6):1-8.

Cohen, et al., (Apr. 19, 2015). "Sepsis: a roadmap for future research." The Lancet Infectious Diseases 15(5):581-614.

Kartal,et al., (Jun. 1, 2012). "Several Cytokines and Protein C Levels with the Apache II Scoring System for Evaluation of Patients with Sepsis." Balkan Medical Journal 29(2):174-178.

O'Dwyer, et al. (Jan. 29, 2008). "The human response to infection is associated with distinct patterns of interleukin 23 and interleukin 27 expression." Intensive Care Medicine 34(4):683-691.

Selberg, et al., (Jan. 2000). "Discrimination of sepsis and systemic inflammatory response syndrome by determination of circulating plasma concentrations of procalcitonin, protein complement 3a and interleukin-6." Critical Care Medicine 28(8):2793-2798.

Wong, et al., (Feb. 2015). "Developing a clinically feasible personalized medicine approach to pediatric septic shock." American Journal of Respiratory and Critical Care Medicine 191(3):309-315.

Extended European Search Report dated Jul. 31, 2015 for European Application No. 13746458.2, filed on Feb. 7, 2013. 7 pages.

Extended European Search Report dated Jul. 31, 2015 for European Application No. 13747279.1, filed on Feb. 7, 2013. 8 pages.

Extended European Search Report dated Apr. 22, 2016 for European Application No. 13833686.2, filed on Aug. 30, 2013. 7 pages.

Extended European Search Report dated Apr. 12, 2017 for European Application No. 14863430.6, filed on Nov. 25, 2014. 9 pages.

International Preliminary Report on Patentability dated Aug. 21, 2014 for PCT International Application No. PCT/US2013/025221, filed on Feb. 7, 2013. 7 pages.

International Preliminary Report on Patentability dated Mar. 12, 2015 for PCT International Application No. PCT/US2013/057711, filed Feb. 7, 2013. 5 pages.

International Preliminary Report on Patentability dated Jun. 9, 2016 for PCT International Application No. PCT/US2014/067438, filed on Nov. 25, 2014. 10 pages.

International Search Report dated May 15, 2013 for PCT Patent International Application No. PCT/US2013/025221, filed Feb. 7, 2013. 13 pages.

\* cited by examiner

TEMPORAL PEDIATRIC SEPSIS BIOMARKER RISK MODEL

RELATED APPLICATION

This application is a national stage application, filed under 35 U.S.C. § 371, of International Application No. PCT/US2014/067438 filed on Nov. 25, 2014, which claims priority to U.S. Provisional Application No. 61/908,613 filed on Nov. 25, 2013, the contents of which are hereby fully incorporated by reference.

CROSS-REFERENCE TO RELATED APPLICATIONS

The present application claims the benefit of priority 35 U.S.C. § 119(e) to U.S. Provisional Application No. 61/908, 613, filed on Nov. 25, 2013, which is hereby incorporated by reference in its entirety.

STATEMENT REGARDING FEDERALLY-SPONSORED RESEARCH

This invention was made with government support under HL 100474, GM064619, GM099773, and TR000077 awarded by the National Institutes of Health (NIH). The government has certain rights in the invention.

FIELD OF THE INVENTION

The invention disclosed herein generally relates to the identification and validation of clinically relevant, quantifiable biomarkers of diagnostic and therapeutic responses for blood, vascular, cardiac, and respiratory tract dysfunction.

BACKGROUND

Septic shock and severe sepsis represent a major public health problem in the United States, despite the development of increasingly powerful antibiotics and advanced forms of intensive care unit-based support modalities (see, e.g., Shanley, T. et al. *Sepsis*, $3^{rd}$ Ed., St. Louis, Mo., Mosby (2006)). Worldwide, septic shock affects millions of adults, killing approximately one in four (see, e.g., Dellinger, R. et al. *Crit. Care Med.* 36:296-327 (2008)). A recent study suggests that the incidence and the mortality rates of septic shock in adults are increasing in the United States (Dombrovskiy, V. et al. *Crit. Care Med.* 35:1244-50 (2007)).

Septic shock is also a major problem in the pediatric age group, as there are ~42,000 cases of pediatric septic shock per year in the United States alone, with a mortality rate of ~10% (see, e.g., Watson, R. et al. *Am. J. Respir. Crit. Care Med.* 167:695-701 (2003)). While the pediatric mortality rate is lower than that of adults, it nonetheless translates to more than 4,000 childhood deaths per year and countless years of lost productivity due to death at a young age. While this high number of pediatric deaths per year from septic shock indicates that more children die per year in the United States from septic shock as the primary cause than those children who die from cancer, funding specifically targeted toward pediatric septic shock is substantially lower than that for pediatric cancer.

Reliable stratification of outcome risk is fundamental to effective clinical practice and clinical research (Marshall *J. Leukoc. Biol.* 83:471-82 (2008)). Risk stratification tools specific for septic shock in pediatric patients would be beneficial at several levels, including stratification for interventional clinical trials, better-informed decision making for individual patients (i.e. prognostication), and as a metric for quality improvement efforts.

SUMMARY

Embodiments of the invention encompass methods of monitoring the therapeutic efficacy of a treatment being administered to a patient with septic shock, the methods including: identifying a pediatric patient with septic shock; obtaining a first sample from the patient at a first time point; analyzing the first sample to determine a first level of at least one biomarker associated with septic shock in pediatric patients; determining whether the level is elevated above a cut-off level, wherein the presence of an elevated level indicates that the patient has an elevated likelihood of being classified as high risk for a poor outcome and the absence of an elevated level indicates that the patient has a reduced likelihood of being classified as high risk for a poor outcome; obtaining a second sample from the patient at a second time point, wherein the second time point occurs after a treatment has been administered to the patient; analyzing the second sample to determine a second level of the at least one biomarker; determining whether the second level is elevated above a cut-off level, wherein the presence of an elevated level indicates that the patient has an elevated likelihood of being classified as high risk for a poor outcome and the absence of an elevated level indicates that the patient has a reduced likelihood of being classified as high risk for a poor outcome; and comparing the patient's risk for a poor outcome at each of the time points to determine if the patient's risk for a poor outcome increased or decreased between the time points, where an increased risk for a poor outcome can indicate that a therapy has had a poor efficacy, and a reduced risk for a poor outcome can indicate that a therapy has had a good efficacy.

Embodiments of the invention encompass the use of methods of monitoring the therapeutic efficacy of a treatment being administered to a patient with septic shock, the methods including: identifying a pediatric patient with septic shock; obtaining a first sample from the patient at a first time point; analyzing the first sample to determine a first level of at least one biomarker associated with septic shock in pediatric patients; determining whether the level is elevated above a cut-off level, wherein the presence of an elevated level indicates that the patient has an elevated likelihood of being classified as high risk for a poor outcome and the absence of an elevated level indicates that the patient has a reduced likelihood of being classified as high risk for a poor outcome; obtaining a second sample from the patient at a second time point, wherein the second time point occurs after a treatment has been administered to the patient; analyzing the second sample to determine a second level of the at least one biomarker; determining whether the second level is elevated above a cut-off level, wherein the presence of an elevated level indicates that the patient has an elevated likelihood of being classified as high risk for a poor outcome and the absence of an elevated level indicates that the patient has a reduced likelihood of being classified as high risk for a poor outcome; and comparing the patient's risk for a poor outcome at each of the time points to determine if the patient's risk for a poor outcome increased or decreased between the time points, where an increased risk for a poor outcome can indicate that a therapy has had a poor efficacy, and a reduced risk for a poor outcome can indicate that a therapy has had a good efficacy in order to treat a pediatric patient with septic shock.

In some embodiments, the first time point can be within the first hour of presentation with septic shock. In some embodiments, the first time point can be within the first 8 hours of presentation with septic shock. In some embodiments, the first time point can be within the first 24 hours of presentation with septic shock. In some embodiments, the second time point can be 24-60 hours after the first time point.

In some embodiments, the method can further include: obtaining a third sample from the patient at a third time point, wherein the third time point occurs after a treatment has been administered to the patient; analyzing the third sample to determine a third level of the at least one biomarker; and determining whether the third level is elevated above a cut-off level. In some embodiments, the first time point can be on the first day the patient presents with septic shock, the second time point can be 12-36 hours after the first time point, and the third time point can be 12-36 hours after the second time point.

In some embodiments, the method can further include: obtaining at least one additional sample(s) from the patient at least one additional time point(s), wherein the at least one additional time point(s) occur after a treatment has been administered to the patient; analyzing the at least one additional sample to determine at least one additional level of the at least one biomarker; and determining whether the at least one additional level is elevated above a cut-off level. In some embodiments, the at least one additional time point occurs within the first 60 hours of presentation with septic shock.

In some embodiments, the at least one biomarker can be selected from the group consisting of CCL3, IL8, and HSPA1B. In some embodiments, the at least one biomarker can be all of CCL3, IL8, and HSPA1B.

In some embodiments, a classification of high risk includes: a) a non-elevated level of CCL3 and an elevated level of IL8 at the first time point, and a highly elevated level of IL8 at the second time point, or b) a highly elevated level of CCL3 at the first time point, and a non-elevated level of IL8 at the second time point, or c) an elevated level of CCL3 and a highly elevated level of IL8 at the first time point, and an elevated level of IL8 at the second time point, or d) an elevated level of CCL3 and a non-highly elevated level of IL8 at the first time point, and elevated levels of IL8 and HSPA1B at the second time point, and a classification of low risk includes: g) non-elevated levels of CCL3 and IL8 at the first time point, or h) a non-elevated level of CCL3 and an elevated level of IL8 at the first time point, and a non-highly elevated level of IL8 at the second time point, or i) a non-highly elevated level of CCL3 at the first time point, and a non-elevated level of IL8 at the second time point, or j) an elevated level of CCL3 and a non-highly elevated level of IL8 at the first time point, and an elevated level of IL8 and a non-elevated level of HSPA1B at the second time point. In some embodiments, a) an elevated level of CCL3 at the first time point corresponds to a serum CCL3 concentration greater than 130 pg/ml, b) a highly elevated level of CCL3 at the first time point corresponds to a serum CCL3 concentration greater than 216 pg/ml, c) an elevated level of IL8 at the first time point corresponds to a serum IL8 concentration greater than 125 pg/ml, d) a highly elevated level of IL8 at the first time point corresponds to a serum IL8 concentration greater than 436 pg/ml, e) an elevated level of IL8 at the second time point corresponds to a serum IL8 concentration greater than 33 pg/ml, f) an elevated level of IL8 at the second time point corresponds to a serum IL8 concentration greater than 123 pg/ml, and g) an elevated level of HSPA1B at the second time point corresponds to a serum HSPA1B concentration greater than 1.20 µg/ml.

In some embodiments, the determination of whether the level(s) of the one or more biomarkers are elevated above a cut-off level includes applying the patient to a decision tree including the one or more biomarkers. In some embodiments, the patient can be applied to the decision tree depicted in FIG. 2, with terminal nodes 3, 5, 7, and 8 corresponding to a classification of high risk and terminal nodes 11, 2, 4, and 6 corresponding to a classification of low risk.

In some embodiments, the determination of whether the level(s) of the one or more biomarkers are elevated can be combined with one or more patient demographic data and/or clinical characteristics and/or results from other tests or indicia of septic shock. In some embodiments, the patient demographic data comprises the age of the patient. In some embodiments, the patient demographic data and/or clinical characteristics and/or results from other tests or indicia of septic shock comprises the septic shock causative organism, the presence or absence of chronic disease, and/or the gender, race, and/or co-morbidities of the patient.

In some embodiments, the determination of whether the level(s) of the one or more biomarkers are elevated can be combined with one or more additional population-based risk scores. In some embodiments, the one or more population-based risk scores include PRISM and/or PIM.

Embodiments of the invention also include methods of providing individualized treatment for a pediatric patient with septic shock, including identifying a pediatric patient with septic shock; obtaining a first sample from the patient at a first time point; analyzing the first sample to determine a first level of at least one biomarker associated with septic shock in pediatric patients; determining whether the level is elevated above a cut-off level, wherein the presence of an elevated level indicates that the patient has an elevated likelihood of being classified as high risk for a poor outcome and the absence of an elevated level indicates that the patient has a reduced likelihood of being classified as high risk for a poor outcome; obtaining a second sample from the patient at a second time point, wherein the second time point occurs after a treatment has been administered to the patient; analyzing the second sample to determine a second level of the at least one biomarker; determining whether the second level is elevated above a cut-off level, wherein the presence of an elevated level indicates that the patient has an elevated likelihood of being classified as high risk for a poor outcome and the absence of an elevated level indicates that the patient has a reduced likelihood of being classified as high risk for a poor outcome; and comparing the patient's risk for a poor outcome at each of the time points to determine if the patient's risk for a poor outcome increased or decreased between the time points, where an increased risk for a poor outcome can indicate that a therapy has had a poor efficacy, and a reduced risk for a poor outcome can indicate that a therapy has had a good efficacy, and further including discontinuing administration of a treatment determined to have had a poor efficacy, thereby providing individualized treatment.

Embodiments of the invention also include the use of methods of providing individualized treatment for a pediatric patient with septic shock, including identifying a pediatric patient with septic shock; obtaining a first sample from the patient at a first time point; analyzing the first sample to determine a first level of at least one biomarker associated with septic shock in pediatric patients; determining whether the level is elevated above a cut-off level, wherein the presence of an elevated level indicates that the patient has an elevated likelihood of being classified as high risk for a poor outcome and the absence of an elevated level indicates that the patient has a reduced likelihood of being classified as high risk for a poor outcome; obtaining a second sample from the patient at a second time point, wherein the second time point occurs after a treatment has been administered to the patient; analyzing the second sample to determine a second level of the at least one biomarker; determining whether the second level is elevated above a cut-off level, wherein the presence of an elevated level indicates that the patient has an elevated likelihood of being classified as high risk for a poor outcome and the absence of an elevated level indicates that the patient has a reduced likelihood of being classified as high risk for a poor outcome; and comparing the patient's risk for a poor outcome at each of the time points to determine if the patient's risk for a poor outcome increased or decreased between the time points, where an increased risk for a poor outcome can indicate that a therapy has had a poor efficacy, and a reduced risk for a poor outcome can indicate that a therapy has had a good efficacy, and further including discontinuing administration of a treatment determined to have had a poor efficacy, thereby providing individualized treatment.

In some embodiments, a therapy determined to have had a poor efficacy can be replaced with at least one high risk therapy. In some embodiments, the at least one high risk therapy includes extracorporeal membrane oxygenation/life support, plasmapheresis, pulmonary artery catheterization, and/or high volume continuous hemofiltration. Embodiments of the invention are also directed to methods of improving an outcome in a pediatric patient with septic shock via replacing a therapy determined to have had a poor efficacy with at least one high risk therapy.

BRIEF DESCRIPTION OF THE DRAWINGS

Those of skill in the art will understand that the drawings, described below, are for illustrative purposes only. The drawings are not intended to limit the scope of the present teachings in any way.

FIG. 1 depicts the classification tree from the derivation cohort (N=225). The classification tree consists of 7 biomarker-based decision rules and 14 daughter nodes. The classification tree includes day 1 and day 3 data for interleukin-8 (IL8) and C-C chemokine ligand 3 (CCL3), and day 3 data heat shock protein 70 kDa 1B (HSPA1B). Each node provides the biomarker serum concentration-based decision rule and the number of subjects with and without complicated course (CC), with the respective rates. For consistency, the serum concentrations of all biomarkers are provided in pg/ml. Terminal nodes (TNs) 1, 2, 4, and 6 are considered low risk nodes, whereas terminal nodes 3, 5, 7, and 8 are considered high-risk terminal nodes. To calculate the diagnostic test characteristics, all subjects in the low risk terminal nodes (n=126) were classified as predicted to not have a complicated course, whereas all subjects in the high risk terminal nodes (n=99) were classified as predicted to have a complicated course.

FIG. 2 depicts the classification tree from the updated model based on the combined derivation and test cohorts (N=299). The classification tree consists of 7 biomarker-based decision rules and 14 daughter nodes. The classification tree includes day 1 and day 3 interleukin-8 (IL8 data), day 1 C-C chemokine ligand 3 (CCL3) data, and day 3 heat shock protein 70 kDa 1B (HSPA1B) data. Each node provides the biomarker serum concentration-based decision rule and the number of subjects with and without a complicated course (CC), with the respective rates. For consistency, the serum concentrations of all stratification biomarkers are provided in pg/ml. Terminal nodes (TNs) 1, 2, 4, and 6 are considered low risk nodes for a complicated course, whereas terminal nodes 3, 5, 7, and 8 are considered high-risk terminal nodes for a complicated course. To calculate the diagnostic test characteristics, all subjects in the low risk terminal nodes (n=168) were classified as predicted to not have a complicated course, whereas all subjects in the high risk terminal nodes (n=131) were classified as predicted to have a complicated course.

DETAILED DESCRIPTION OF THE INVENTION

All references cited herein are incorporated by reference in their entirety. Also incorporated herein by reference in their entirety include: U.S. Patent Application No. 61/595,996, BIOMARKERS OF SEPTIC SHOCK, filed on Feb. 7, 2012; U.S. Provisional Application No. 61/721,705, A MULTI-BIOMARKER-BASED OUTCOME RISK STRATIFICATION MODEL FOR ADULT SEPTIC SHOCK, filed on Nov. 2, 2012; International Patent Application No. PCT/US13/25223, A MULTI-BIOMARKER-BASED OUTCOME RISK STRATIFICATION MODEL FOR PEDIATRIC SEPTIC SHOCK, filed on Feb. 7, 2013; and International Patent Application No. PCT/US13/25221, A MULTI-BIOMARKER-BASED OUTCOME RISK STRATIFICATION MODEL FOR ADULT SEPTIC SHOCK, filed on Feb. 7, 2013.

Unless otherwise noted, terms are to be understood according to conventional usage by those of ordinary skill in the relevant art.

As used herein, the term "sample" encompasses a sample obtained from a subject or patient. The sample can be of any biological tissue or fluid. Such samples include, but are not limited to, sputum, saliva, buccal sample, oral sample, blood, serum, mucus, plasma, urine, blood cells (e.g., white cells), circulating cells (e.g. stem cells or endothelial cells in the blood), tissue, core or fine needle biopsy samples, cell-containing body fluids, free floating nucleic acids, urine, stool, peritoneal fluid, and pleural fluid, tear fluid, or cells therefrom. Samples can also include sections of tissues such as frozen or fixed sections taken for histological purposes or microdissected cells or extracellular parts thereof. A sample to be analyzed can be tissue material from a tissue biopsy obtained by aspiration or punch, excision or by any other surgical method leading to biopsy or resected cellular material. Such a sample can comprise cells obtained from a subject or patient. In some embodiments, the sample is a body fluid that include, for example, blood fluids, serum, mucus, plasma, lymph, ascitic fluids, gynecological fluids, or urine but not limited to these fluids. In some embodiments, the sample can be a non-invasive sample, such as, for example, a saline swish, a buccal scrape, a buccal swab, and the like.

As used herein, "blood" can include, for example, plasma, serum, whole blood, blood lysates, and the like.

As used herein, the term "assessing" includes any form of measurement, and includes determining if an element is present or not. The terms "determining," "measuring," "evaluating," "assessing" and "assaying" can be used interchangeably and can include quantitative and/or qualitative determinations.

As used herein, the term "monitoring" with reference to septic shock refers to a method or process of determining the severity or degree of septic shock or stratifying septic shock based on risk and/or probability of mortality. In some embodiments, monitoring relates to a method or process of determining the therapeutic efficacy of a treatment being administered to a patient.

As used herein, "outcome" can refer to the primary outcome studied, typically 28-day survival/mortality. The importance of survival/mortality in the context of pediatric septic shock is readily evident. The common choice of 28 days was based on the fact that 28-day mortality is a standard primary endpoint for interventional clinical trials involving critically ill patients. In some embodiments, an increased risk for a poor outcome indicates that a therapy has had a poor efficacy, and a reduced risk for a poor outcome indicates that a therapy has had a good efficacy.

As used herein, "outcome" can also refer to the secondary outcome studied, namely resolution of organ failure after 14 days or 28 days or limb loss. Although mortality/survival is obviously an important outcome, survivors have clinically relevant short- and long-term morbidities that impact quality of life, which are not captured by the dichotomy of "alive" or "dead." In the absence of a formal, validated quality of life measurement tool for survivors of pediatric septic shock, resolution of organ failure was tracked as a secondary outcome measure. Specifically, the presence or absence of new organ failure over two timeframes was tracked: 14 days after admission and 28 days after admission. Patients having organ failure beyond 28 days are likely to survive with significant morbidities having negative consequences for quality of life. Organ failure was defined based on published and well-accepted criteria for the pediatric population (Goldstein, B. et al. *Pediatr. Crit. Care Med.* 6:208 (2005)). Specifically, cardiovascular, respiratory, renal, hepatic, hematologic, and neurologic failure were tracked. In addition, limb loss was tracked as a secondary outcome. Although limb loss is not a true "organ failure," it is an important consequence of pediatric septic shock with obvious impact on quality of life.

As used herein, the terms "predicting outcome" and "outcome risk stratification" with reference to septic shock refers to a method or process of prognosticating a patient's risk of a certain outcome. In some embodiments, predicting an outcome relates to monitoring the therapeutic efficacy of a treatment being administered to a patient. In some embodiments, predicting an outcome relates to determining a relative risk of mortality. Such mortality risk can be high risk, moderate risk, moderate-high risk, moderate-low risk, or low risk. Alternatively, such mortality risk can be described simply as high risk or low risk, corresponding to high risk of death or high likelihood of survival, respectively. As related to the terminal nodes of the decision trees described herein, a "high risk terminal node" corresponds to a high mortality probability, whereas a "low risk terminal node" corresponds to a low mortality probability.

As used herein, the term "high risk clinical trial" refers to one in which the test agent has "more than minimal risk" (as defined by the terminology used by institutional review boards, or IRBs). In some embodiments, a high risk clinical trial is a drug trial.

As used herein, the term "low risk clinical trial" refers to one in which the test agent has "minimal risk" (as defined by the terminology used by IRBs). In some embodiments, a low risk clinical trial is one that is not a drug trial. In some embodiments, a low risk clinical trial is one that that involves the use of a monitor or clinical practice process. In some embodiments, a low risk clinical trial is an observational clinical trial.

As used herein, the terms "modulated" or "modulation," or "regulated" or "regulation" and "differentially regulated" can refer to both up regulation (i.e., activation or stimulation, e.g., by agonizing or potentiating) and down regulation (i.e., inhibition or suppression, e.g., by antagonizing, decreasing or inhibiting), unless otherwise specified or clear from the context of a specific usage.

As used herein, the term "subject" refers to any member of the animal kingdom. In some embodiments, a subject is a human patient. In some embodiments, a subject is a pediatric patient. In some embodiments, a pediatric patient is a patient under 18 years of age, while an adult patient is 18 or older.

As used herein, the terms "treatment," "treating," "treat," and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition.

As used herein, the term "marker" or "biomarker" refers to a biological molecule, such as, for example, a nucleic acid, peptide, protein, hormone, and the like, whose presence or concentration can be detected and correlated with a known condition, such as a disease state. It can also be used to refer to a differentially expressed gene whose expression pattern can be utilized as part of a predictive, prognostic or diagnostic process in healthy conditions or a disease state, or which, alternatively, can be used in methods for identifying a useful treatment or prevention therapy.

As used herein, the term "expression levels" refers, for example, to a determined level of biomarker expression. The term "pattern of expression levels" refers to a determined level of biomarker expression compared either to a reference (e.g. a housekeeping gene or inversely regulated genes, or other reference biomarker) or to a computed average expression value (e.g. in DNA-chip analyses). A pattern is not limited to the comparison of two biomarkers but is more related to multiple comparisons of biomarkers to reference biomarkers or samples. A certain "pattern of expression levels" can also result and be determined by comparison and measurement of several biomarkers as disclosed herein and display the relative abundance of these transcripts to each other.

As used herein, a "reference pattern of expression levels" refers to any pattern of expression levels that can be used for the comparison to another pattern of expression levels. In some embodiments of the invention, a reference pattern of expression levels is, for example, an average pattern of expression levels observed in a group of healthy or diseased individuals, serving as a reference group.

As used herein, the term "decision tree" refers to a standard machine learning technique for multivariate data analysis and classification. Decision trees can be used to derive easily interpretable and intuitive rules for decision support systems.

A pediatric sepsis biomarker risk model, called PERSEVERE (PEdiatRic SEpsis biomarkEr Risk modEl) has been previously derived and validated (Wong H. et al., *Crit. Care* 16:R174 (2012)). PERSEVERE assigns a 28-day mortality probability for children with septic shock based on a panel of five biomarkers and age. The biomarkers that were used to derive PERSEVERE were measured from serum samples obtained during the first 24 hours of presentation to the pediatric intensive care unit (PICU) with septic shock, which is a clinically relevant time period for assigning mortality risk in this heterogeneous population.

While the ability of PERSEVERE to assign a reliable mortality probability during the initial stages of septic shock has inherent utility at multiple levels, it fails to consider temporal changes in biomarker levels and how these temporal changes may further inform the estimation of risk for poor outcome. This is important because the natural history of septic shock is intrinsically dynamic and subject to change in response to therapy (Hanna W. and Wong H., *Crit. Care Clin.* 29:203-222 (2013); Wong H., *Pediatr. Res.* 73:564-569 (2013); Wynn J. et al., *Pediatrics* 125:1031-1041 (2010)). Consequently, the risk for poor outcome also changes over time, and it is biologically plausible that temporal changes in the PERSEVERE biomarkers may reflect this change.

The results described herein relate to the derivation of a temporal version of PERSEVERE (tPERSEVERE). This model incorporates biomarker measurements at two time points, specifically the first and third day following presentation, during the initial three days of illness in order to estimate the probability of a "poor outcome" or a "complicated course," defined as persistence of ≥2 organ failures at seven days after meeting criteria for septic shock, or death within 28 days. The prognostic accuracy of tPERSEVERE in an independent test cohort was subsequently tested.

This model was developed from a prospective, multicenter pediatric septic shock clinical and biological database, at nineteen pediatric institutions, with a derivation cohort (n=225) and a test cohort (n=72) of patients with septic shock. Biomarkers were measured in the derivation cohort using serum samples obtained during day 1 and day 3 of septic shock. Classification and Regression Tree (CART) analysis was used to derive a model to estimate the risk of a complicated course. The derived model was tested in the test cohort and subsequently updated using the combined derivation and test cohorts. The derived model had a sensitivity for a complicated course of 90% (95% CI 78-96), specificity was 70% (62-77), positive predictive value was 47% (37-58), and negative predictive value was 96% (91-99). The area under the receiver operating characteristic curve was 0.85 (0.79-0.90). Similar test characteristics were observed in the test cohort. The updated model had a sensitivity of 91% (81-96), a specificity of 70% (64-76), a positive predictive value of 47% (39-56), and a negative predictive value of 96% (92-99).

tPERSEVERE was found to accurately and reliably estimate the risk of a complicated course in a heterogeneous cohort of children with septic shock. The study subjects were drawn from multiple centers and pooled from four distinct databanks, thus adding substantial variability with regard to pathology and therapeutic interventions. Despite the concern that such heterogeneity might diminish the accuracy of predictions, tPERSEVERE was found to perform reliably, indicating that tPERSEVERE will be generalizable upon further testing.

The positive and negative predictive values of a diagnostic test are influenced by the prevalence of the outcome of interest (Kaplan J. et al. *Pediatr. Crit. Care Med.* 12:165-73 (2011)). In this study, the prevalence of a complicated course was about 23%, so one would expect that the positive predictive value would be lower than the negative predictive value. Further, if one assumes that therapeutic interventions are beneficial and can ameliorate the risk of a poor outcome, then some of the false positives (which lower the positive predictive value and specificity) likely represent patients in whom the predicted poor outcome was prevented by therapeutic interventions.

The high sensitivity allows one to reliably identify patients at risk for a poor outcome, while the high negative predictive value allows one to identify those who are low risk. A dichotomous interpretation of the model is that it can be used to divide a heterogeneous cohort of children with septic shock into two groups that differ by a factor of ten in the probability of a poor outcome. An alternative interpretation of the model is to view each terminal node individually, which allows for the assignment of a range of probabilities for a complicated course.

The modeling procedures used in this derivation were focused on a composite outcome variable, complicated course, whereas the previous study focused on 28-day mortality (Wong H. et al., *Crit. Care* 16:R174 (2012)). There are two primary reasons for this change in focus. First, while 28-day mortality is an important outcome variable, mortality alone does not fully capture all septic shock-associated morbidity. Organ failure has been associated with poor functional outcomes in septic shock survivors (Typpo K. et al., *Pediatr. Crit. Care Med.* 10:562-570 (2009)); therefore, the composite variable used in this study has been recently proposed as a clinically relevant study endpoint (Mickiewicz B. et al., *Am. J. Respir. Crit. Care Med.* 187:967-976 (2013); Abulebda A. et al., *Crit. Care Med.* In Press (2013)). Second, the incidence of mortality in the study cohorts was too low for reliable modeling. Importantly, the five false negative subjects in the derivation cohort and the three false negatives in the test cohort all survived. This indicates that tPERSEVERE has very high reliability for predicting mortality, even though it was derived to estimate the risk of a complicated course.

The performance of PERSEVERE was previously compared to that of PRISM, and it was found that PERSEVERE outperformed PRISM (Wong H. et al., *Crit. Care* 16:R174 (2012); Wong H. et al., *PloS One* in press (2014)). tPERSEVERE has presently not been compared to PRISM because the latter is not intended to be used as a temporal scoring system.

tPERSEVERE can be used as an adjunct to traditional physiological parameters for monitoring therapeutic interventions in children with septic shock. Assuming that the risk of a complicated course is modified by therapy, tPERSEVERE provides an objective readout of therapeutic effectiveness by comparison to the baseline risk predicted by PERSEVERE. A changing risk, reflected by changing biomarkers, can even serve as a surrogate outcome variable in Phase 1 or 2 interventional clinical trials.

In the initially derived tPERSEVERE, 49% of the derivation cohort subjects and 63% of the test cohort subjects occupy terminal nodes 1 and 8, which are dependent only on day 1 data. However, in the updated model, there is only one terminal node that is dependent exclusively on day 1 data (TN1), and only 28% of the subjects occupy this node. The remaining terminal nodes are informed by both day 1 and day 3 biomarker data.

In conclusion, a temporal version of PERSEVERE (tPERSEVERE) has been derived, tested, and updated. tPERSE- VERE can be used to stratify patients or to monitor the therapeutic efficacy of a treatment being administered to a patient with septic shock. tPERSEVERE can be used as an adjunct to physiological assessments for monitoring the efficacy of therapeutic interventions in children with septic shock, or to serve as a surrogate outcome variable in clinical trials.

Use of Multiple Time Points

The temporal biomarker-based risk model, as described herein, uses data from 2 or more time points in order to monitor the therapeutic efficacy of a treatment being administered to a patient with septic shock. As will be appreciated by those skilled in the art, such a temporal biomarker-based risk model can be designed to use any number of time points greater than 1, with any interval of time between additional time points. In practice, those implementing the temporal biomarker-based risk model can select an appropriate number of time points at which to acquire data, as well as appropriate intervals of time between additional time points.

In some embodiments, the temporal biomarker-based risk model can use 2 or more time points. In some embodiments, the temporal biomarker-based risk model can use 3 or more time points. In some embodiments, the temporal biomarker-based risk model can use 4 or more time points. In some embodiments, the temporal biomarker-based risk model can use 5 or more time points. In some embodiments, the temporal biomarker-based risk model can use 6 or more, 7 or more, 8 or more, 9 or more, or 10 or more time points. In some embodiments, the temporal biomarker-based risk model can use more than 15 time points.

In some embodiments, the first time point is within the first hour of presentation with septic shock. In some embodiments, the first time point is within the first 8 hours of presentation with septic shock. In some embodiments, the first time point is within the first 24 hours of presentation with septic shock. In some embodiments, the first time point is within the first 36 hours of presentation with septic shock. In some embodiments, the first time point is within the first 48 hours of presentation with septic shock. In some embodiments, the first time point is after the first 48 hours of presentation with septic shock.

The temporal biomarker-based risk model uses 2 or more time points, wherein each additional time point occurs after the time point that immediately precedes it. In some embodiments, the additional time point occurs after a treatment has been administered to the patient. In some embodiments, the additional time point is within 1 hour of the time point that immediately precedes it. In some embodiments, the additional time point is between 1-12 hours after the time point that immediately precedes it. In some embodiments, the additional time point is between 12-24 hours after the time point that immediately precedes it. In some embodiments, the additional time point is between 24-60 hours after the time point that immediately precedes it. In some embodiments, the additional time point is more than 60 hours after the time point that immediately precedes it.

The second time point occurs after the first time point. In some embodiments, the second time point occurs after a treatment has been administered to the patient. In some embodiments, the second time point is within 1 hour of the first time point. In some embodiments, the second time point is between 1-12 hours after the first time point. In some embodiments, the second time point is between 12-24 hours after the first time point. In some embodiments, the second time point is between 24-60 hours after the first time point. In some embodiments, the second time point is more than 60 hours after the first time point.

In embodiments where the temporal biomarker-based risk model uses 3 or more time points, the third time point occurs after the second time point. In some embodiments, the third time point occurs after a treatment has been administered to the patient. In some embodiments, the third time point is within 1 hour of the second time point. In some embodiments, the third time point is between 1-12 hours after the second time point. In some embodiments, the third time point is between 12-24 hours after the second time point. In some embodiments, the third time point is between 24-60 hours after the second time point. In some embodiments, the third time point is more than 60 hours after the second time point.

In embodiments where the temporal biomarker-based risk model uses 4 or more time points, the fourth time point occurs after the third time point. In some embodiments, the fourth time point occurs after a treatment has been administered to the patient. In some embodiments, the fourth time point is within 1 hour of the third time point. In some embodiments, the fourth time point is between 1-12 hours after the third time point. In some embodiments, the fourth time point is between 12-24 hours after the third time point. In some embodiments, the fourth time point is between 24-60 hours after the third time point. In some embodiments, the fourth time point is more than 60 hours after the third time point.

In embodiments where the temporal biomarker-based risk model uses 5 or more time points, the fifth time point occurs after the fourth time point. In some embodiments, the fifth time point occurs after a treatment has been administered to the patient. In some embodiments, the fifth time point is within 1 hour of the fourth time point. In some embodiments, the fifth time point is between 1-12 hours after the fourth time point. In some embodiments, the fifth time point is between 12-24 hours after the fourth time point. In some embodiments, the fifth time point is between 24-60 hours after the fourth time point. In some embodiments, the fifth time point is more than 60 hours after the fourth time point.

Additional Patient Information

The demographic data, clinical characteristics, and/or results from other tests or indicia of septic shock specific to a pediatric patient with septic shock can affect the patient's outcome risk. Accordingly, such demographic data, clinical characteristics, and/or results from other tests or indicia of septic shock can be incorporated into the methods described herein which allow for stratification of individual pediatric patients in order to determine the patient's outcome risk. Such demographic data, clinical characteristics, and/or results from other tests or indicia of septic shock can also be used in combination with the methods described herein which allow for stratification of individual pediatric patients in order to determine the patient's outcome risk.

Such pediatric patient demographic data can include, for example, the patient's age, race, gender, and the like.

In some embodiments, the temporal biomarker-based risk model described herein can incorporate the patient's age to determine an outcome risk. In some embodiments, the temporal biomarker-based risk model described herein can incorporate the patient's race to determine an outcome risk. In some embodiments, the temporal biomarker-based risk model described herein can incorporate the patient's gender to determine an outcome risk.

In some embodiments, the temporal biomarker-based risk model described herein can be used in combination with the patient's age to determine an outcome risk. In some embodiments, the temporal biomarker-based risk model described herein can be used in combination with the patient's race to determine an outcome risk. In some embodiments, the temporal biomarker-based risk model described herein can be used in combination with the patient's gender to determine an outcome risk.

Such patient clinical characteristics and/or results from other tests or indicia of septic shock can include, for example, the patient's co-morbidities and/or septic shock causative organism, and the like.

Patient co-morbidities can include, for example, acute lymphocytic leukemia, acute myeloid leukemia, aplastic anemia, atrial and ventricular septal defects, bone marrow transplantation, caustic ingestion, chronic granulomatous disease, chronic hepatic failure, chronic lung disease, chronic lymphopenia, chronic obstructive pulmonary disease (COPD), congestive heart failure (NYHA Class IV CHF), Cri du Chat syndrome, cyclic neutropenia, developmental delay, diabetes, DiGeorge syndrome, Down syndrome, drowning, end stage renal disease, glycogen storage disease type 1, hematologic or metastatic solid organ malignancy, hemophagocytic lymphohistiocytosis, hepatoblastoma, heterotaxy, hydrocephalus, hypoplastic left heart syndrome, IPEX Syndrome, kidney transplant, Langerhans cell histiocytosis, liver and bowel transplant, liver failure, liver transplant, medulloblastoma, metaleukodystrophy, mitochondrial disorder, multiple congenital anomalies, multivisceral transplant, nephrotic syndrome, neuroblastoma, neuromuscular disorder, obstructed pulmonary veins, Pallister Killian syndrome, Prader-Willi syndrome, requirement for chronic dialysis, requirement for chronic steroids, retinoblastoma, rhabdomyosarcoma, rhabdosarcoma, sarcoma, seizure disorder, severe combined immune deficiency, short gut syndrome, sickle cell disease, sleep apnea, small bowel transplant, subglottic stenosis, tracheal stenosis, traumatic brain injury, trisomy 18, type 1 diabetes mellitus, unspecified brain tumor, unspecified congenital heart disease, unspecified leukemia, VATER Syndrome, Wilms tumor, and the like. Any one or more of the above patient co-morbidities can be indicative of the presence or absence of chronic disease in the patient.

Septic shock causative organisms can include, for example, *Acinetobacter baumannii*, Adenovirus, *Bacteroides* species, *Candida* species, *Capnotyophaga jenuni*, *Cytomegalovirus*, *Enterobacter cloacae*, *Enterococcus faecalis*, *Escherichia coli*, *Herpes simplex* virus, *Human metapneumovirus*, Influenza A, *Klebsiella pneumonia*, *Micrococcus* species, mixed bacterial infection, *Moraxella catarrhalis*, *Neisseria meningitides*, Parainfluenza, *Pseudomonas* species, *Serratia marcescens*, *Staphylococcus aureus*, *Streptococcus agalactiae*, *Streptococcus milleri*, *Streptococcus pneumonia*, *Streptococcus pyogenes*, unspecified gram negative rods, unspecified gram positive cocci, and the like.

In some embodiments, the temporal biomarker-based risk model described herein can incorporate the patient's co-morbidities to determine an outcome risk. In some embodiments, the temporal biomarker-based risk model described herein can incorporate the patient's septic shock causative organism to determine an outcome risk.

In some embodiments, the temporal biomarker-based risk model described herein can be used in combination with the patient's co-morbidities to determine an outcome risk. In some embodiments, the temporal biomarker-based risk model described herein can be used in combination with the patient's septic shock causative organism to determine an outcome risk.

Population-Based Risk Scores

A number of models that generate mortality prediction scores based on physiological variables have been developed to date. These can include the APACHE, PRISM, Pediatric Index of Mortality (PIM), and/pediatric logistic organ dysfunction (PELOD) models, and the like. The APACHE model considered can be APACHE I, APACHE II, APACHE III, APACHE IV, or a subsequent iteration of APACHE.

Such models can be very effective for estimating population-based outcome risks but are not intended for stratification of individual patients. The methods described herein which allow for stratification of individual patients can be used alone or in combination with one or more existing population-based risk scores.

In some embodiments, the temporal biomarker-based risk model described herein can be used with one or more additional population-based risk scores. In some embodiments, the temporal biomarker-based risk model described herein can be used in combination with APACHE. In some embodiments, the temporal biomarker-based risk model described herein can be used in combination with PRISM. In some embodiments, the temporal biomarker-based risk model described herein can be used in combination with PIM. In some embodiments, the temporal biomarker-based risk model described herein can be used in combination with PELOD. In some embodiments, the temporal biomarker-based risk model described herein can be used in combination with a population-based risk score other than APACHE, PRISM, PELOD, and PRISM.

High Risk Therapies

High risk, invasive therapeutic and support modalities can be used to treat septic shock. The methods described herein which allow for the patient's outcome risk to be determined can help inform clinical decisions regarding the application of high risk therapies to specific pediatric patients, based on the patient's outcome risk.

High risk therapies include, for example, extracorporeal membrane oxygenation/life support, plasmapheresis, pulmonary artery catheterization, high volume continuous hemofiltration, and the like.

In some embodiments, individualized treatment can be provided to a pediatric patient by selecting a pediatric patient classified as high risk by the methods described herein for one or more high risk therapies. In some embodiments, individualized treatment can be provided to a pediatric patient by excluding a pediatric patient classified as low risk from one or more high risk therapies.

Certain embodiments of the invention include using quantification data from a gene-expression analysis and/or from a mRNA analysis, from a sample of blood, urine, saliva, broncho-alveolar lavage fluid, or the like. Embodiments of the invention include not only methods of conducting and interpreting such tests but also include reagents, kits, assays, and the like, for conducting the tests.

Diagnostic-testing procedure performance is commonly described by evaluating control groups to obtain four critical test characteristics, namely positive predictive value (PPV), negative predictive value (NPV), sensitivity, and specificity, which provide information regarding the effectiveness of the test. The PPV of a particular diagnostic test represents the proportion of positive tests in subjects with the condition of interest (i.e. proportion of true positives); for tests with a high PPV, a positive test indicates the presence of the condition in question. The NPV of a particular diagnostic test represents the proportion of negative tests in subjects without the condition of interest (i.e. proportion of true negatives); for tests with a high NPV, a negative test indicates the absence of the condition. Sensitivity represents the proportion of subjects with the condition of interest who will have a positive test; for tests with high sensitivity, a positive test indicates the presence of the condition in question. Specificity represents the proportion of subjects without the condition of interest who will have a negative test; for tests with high specificity, a negative test indicates the absence of the condition.

The threshold for the disease state can alternatively be defined as a 1-D quantitative score, or diagnostic cutoff, based upon receiver operating characteristic (ROC) analysis. The quantitative score based upon ROC analysis can be used to determine the specificity and/or the sensitivity of a given diagnosis based upon subjecting a patient to the decision tree described herein in order to predict an outcome for a pediatric patient with septic shock.

The correlations disclosed herein, between pediatric patient septic shock biomarker levels and/or mRNA levels and/or gene expression levels, provide a basis for conducting a diagnosis of septic shock, or for conducting a stratification of patients with septic shock, or for enhancing the reliability of a diagnosis of septic shock by combining the results of a quantification of a septic shock biomarker with results from other tests or indicia of septic shock. For example, the results of a quantification of one biomarker could be combined with the results of a quantification of one or more additional biomarker, cytokine, mRNA, or the like. Thus, even in situations in which a given biomarker correlates only moderately or weakly with septic shock, providing only a relatively small PPV, NPV, specificity, and/or sensitivity, the correlation can be one indicium, combinable with one or more others that, in combination, provide an enhanced clarity and certainty of diagnosis. Accordingly, the methods and materials of the invention are expressly contemplated to be used both alone and in combination with other tests and indicia, whether quantitative or qualitative in nature.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Derivation Cohort Study Subjects

Seventeen institutions contributed biological specimens and clinical data to a central repository, with approval from the Institutional Review Boards of each participating institution. Data collection methods have been previously described (Wong H. et al., *Crit. Care* 16:R174 (2012)). Children ≤10 years of age admitted to the PICU and meeting pediatric-specific criteria for septic shock were eligible for enrollment. After informed consent from parents or legal guardians, serum samples were obtained within 24 hours of initial presentation to the PICU with septic shock; these are referred to as "day 1" samples. Forty-eight hours after obtaining day 1 samples, a second serum sample was obtained; these are referred to as "day 3" samples. Of the 355 subjects in the original PERSEVERE derivation and validation cohorts, there were 225 with biomarker data available for both day 1 and day 3. The current analysis included these 225 subjects, all of whom were enrolled between May 2002 and August 2010.

Example 2

Test Cohort Study Subjects

The test cohort subjects were pooled from four sources, with approval from the respective Institutional Review Boards. Thirty-three subjects were included from an ongoing genomics study in pediatric septic shock being conducted at 17 participating institutions (Cvijanovich N. et al., *Physiol. Genomics* 34:127-134 (2008); Shanley T. et al., *Mol. Med.* 13:495-508 (2007); Wong H. et al., *Crit. Care Med.* 37:1558-1566 (2009); Wong H. et al., *BMC Med.* 7:34 (2009); Wong H. et al., *Physiol. Genomics* 30:146-155 (2007); Wynn J. et al., *Mol. Med.* 17:1146-1156 (2011); Basu R. et al., *Crit. Care* 15:R273 (2011); Wong H. et al., *Crit. Care Med.* 39:2511-2517 (2011); Wong H. et al., *Pediatr. Crit. Care Med.* 11:349-355 (2010); Wong H. et al., *Am. J. Resp. Crit. Care Med.* 178:276-282 (2008)). The enrollment criteria were identical to those for the derivation cohort. The current analysis included subjects enrolled between September 2011 and May 2013.

Eleven subjects were included from among those enrolled in a quality improvement program at one institution. The institution uses PERSEVERE to benchmark septic shock outcomes for all patients admitted to the PICU with septic shock. Enrollment procedures were identical to those described above, except that there was no age restriction, and the Institutional Review Board granted permission for waiver of informed consent. Serum samples were collected from residual blood samples in the clinical laboratory. Subjects from this source were enrolled between September 2012 and May 2013.

Nineteen subjects (age range: 8 days to 18 years) were participants in a prospective, observational study at Ann & Robert H. Lurie Children's Hospital of Chicago, Chicago, Ill., evaluating nitric oxide metabolism and mitochondrial function in children with septic shock (Weiss S. et al., *Pediatr. Crit. Care Med.* 13:e210-218 (2012)). Of the 30 subjects with septic shock enrolled in that study, 19 had serum samples available for analysis. The current analysis included subjects enrolled between May 2009 and June 2010.

Eleven subjects (age range: 2 to 20 years old) were participants in a prospective, observational study at Yale-New Haven Children's Hospital, New Haven, Conn., evaluating angiopoietin levels in children with septic shock (Giuliano J. et al., *Pediatr. Crit. Care Med*. In Press (2013)). Of the 17 subjects with septic shock enrolled in that study, 11 had serum samples available for analysis. The current analysis included subjects enrolled between September 2009 and December 2011.

Example 3

Study Procedures

For all studies, annotated clinical and laboratory data were collected daily while the participant was in the PICU. Illness severity was calculated prospectively using the Pediatric Risk of Mortality (PRISM) score (Pollack M. et al., *J. Pediatr.* 131:575-581 (1997)). The number of organ failures during the initial 7 days of PICU admission was recorded using pediatric-specific criteria (Goldstein B. et al., *Pediatr. Crit. Care Med.* 6:2-8 (2005)). All-cause mortality was tracked for 28 days after meeting criteria for septic shock. The composite endpoint used herein termed "complicated course", was defined as persistence of two or more organ failures at seven days after meeting criteria for septic shock, or death within 28 days of presentation (Mickiewicz B. et al., *Am. J. Respir. Crit. Care Med.* 187:967-976 (2013); Abulebda A. et al., *Crit. Care Med.* In Press (2013); Xiao W. et al., *J. Exp. Med.* 208:2581-2590 (2011)).

Example 4

Biomarkers

PERSEVERE includes C-C chemokine ligand 3 (CCL3), interleukin 8 (IL8), heat shock protein 70 kDa 1B (HSPA1B), granzyme B (GZMB), and matrix metallopeptidase 8 (MMP8). Serum concentrations of these biomarkers were measured using a multi-plex magnetic bead platform (MILLIPLEX™ MAP) designed for this project by the EMD Millipore Corporation (Billerica, Mass.). Biomarker concentrations were measured in a Luminex® 100/200 System (Luminex Corporation, Austin, Tex.), according the manufacturers' specifications. Assay performance data were previously published (Wong H. et al., *Crit. Care* 16:R174 (2012)).

Example 5

Statistical Analysis

Initially, data were described using medians, interquartile ranges, frequencies, and percentages. Comparisons between groups used the Mann-Whitney U-test, Chi-square, or Fisher's Exact tests as appropriate. Descriptive statistics and comparisons used SigmaStat Software (Systat Software, Inc., San Jose, Calif.).

CART analysis was used to derive tPERSEVERE (Salford Predictive Modeler v6.6, Salford Systems, San Diego, Calif.) (Wong H. et al., *Crit. Care* 16:R174 (2012); Che D. et al., *Adv. Exp. Med. Biol.* 696:191-199 (2011); Muller R. et al., *Clin. Chim. Acta* 394:1-6 (2008)). The primary outcome variable for the modeling procedures was complicated course. The absolute day 1 and day 3 biomarker values, the percentage change in biomarker values from day 1 to day 3, and age were considered in the modeling procedures. Performance of the derived model was reported using diagnostic test statistics with 95% confidence intervals computed using the score method as implemented by the VassarStats Website for Statistical Computation (Computation VWfS, found at http <colon slash slash> faculty <dot> vassar <dot> edu <slash> lowry <slash> VassarStats <dot> html).

Example 6

Deriving Tpersevere

Table 1 shows the demographic and clinical characteristics of the derivation cohort (n=225). The 52 (23%) subjects with a complicated course had a higher median PRISM score and were less likely to have a causative organism isolated compared to the 173 subjects with a non-complicated course. No other differences were observed.

TABLE 1

Demographics and clinical characteristics of the derivation and test cohorts.

| | Derivation Cohort | | | Test Cohort | | |
|---|---|---|---|---|---|---|
| | All | Non-Complicated Course | Complicated Course | All | Non-Complicated Course | Complicated Course |
| N | 225 | 173 | 52 | 74 | 58 | 16 |
| Mortality (%) | 7 | n/a | n/a | 5 | n/a | n/a |
| Median age years (IQR) | 2.3 (0.8-5.6) | 2.4 (1.0-6.0) | 1.5 (0.7-4.4) | 5.7 (1.7-12.2)[3] | 5.7 (1.7-12.2) | 5.8 (1.1-14.1) |
| Median PRISM score (IQR)[1] | 14 (9-21) | 12 (8-18) | 21 (12-26)[2] | 11 (9-19) | 11 (7-19) | 14 (11-20) |
| # of males (%) | 141 (63) | 105 (61) | 36 (69) | 37 (50) | 31 (53) | 6 (38)[3] |
| # of females (%) | 84 (37) | 68 (39) | 16 (31) | 37 (50) | 27 (47) | 10 (62) |
| # for race (%) | | | | | | |
| Caucasian | 160 (71) | 126 (73) | 34 (65) | 50 (68) | 38 (66) | 12 (75) |
| African American | 37 (16) | 28 (16) | 9 (17) | 7 (9) | 5 (9) | 2 (13) |
| Other | 13 (6) | 9 (5) | 4 (8) | 1 (1) | 1 (2) | 0 (0) |
| Unreported | 15 (7) | 10 (6) | 5 (10) | 16 (22)[3] | 14 (24) | 2 (13) |
| # with gram (+) bacteria (%) | 61 (27) | 43 (25) | 18 (35) | 20 (27) | 14 (24) | 6 (38) |
| # with gram (−) bacteria (%) | 64 (28) | 45 (26) | 19 (37) | 14 (19) | 10 (17) | 4 (25) |
| # with viral infection (%) | 23 (10) | 15 (9) | 8 (15) | 3 (4) | 3 (5) | 0 (0) |
| # with fungal infection (%) | 3 (1) | 2 (1) | 1 (2) | 3 (4) | 3 (5) | 0 (0) |
| # with no organism isolated (%) | 82 (36) | 71 (41) | 11 (21)[2] | 37 (50)[3] | 31 (53) | 6 (38) |

TABLE 1-continued

Demographics and clinical characteristics of the derivation and test cohorts.

|  | Derivation Cohort | | | Test Cohort | | |
| --- | --- | --- | --- | --- | --- | --- |
|  | All | Non-Complicated Course | Complicated Course | All | Non-Complicated Course | Complicated Course |
| # with any co-morbidity (%) | 98 (44) | 78 (45) | 20 (38) | 12 (16)[3] | 10 (17) | 2 (13) |
| # with malignancy (%) | 16 (7) | 14 (8) | 2 (4) | 0 (0)[3] | 0 (0) | 0 (0) |
| # with immune suppression (%)[4] | 32 (14) | 28 (16) | 4 (8) | 0 (0)[3] | 0 (0) | 0 (0) |

[1]Nineteen subjects (15 with a non-complicated course and 4 with a complicated course) in the test cohort did not have available PRISM scores.
[2]$p < 0.05$ vs. respective subjects with a non-complicated course.
[3]$p < 0.05$ vs. derivation cohort.
[4]Refers to patients with immune suppression not related to cancer (for example, those receiving immune suppressive medication for solid organ or bone marrow transplantation, or those with a primary immune deficiency).

Figure 1:
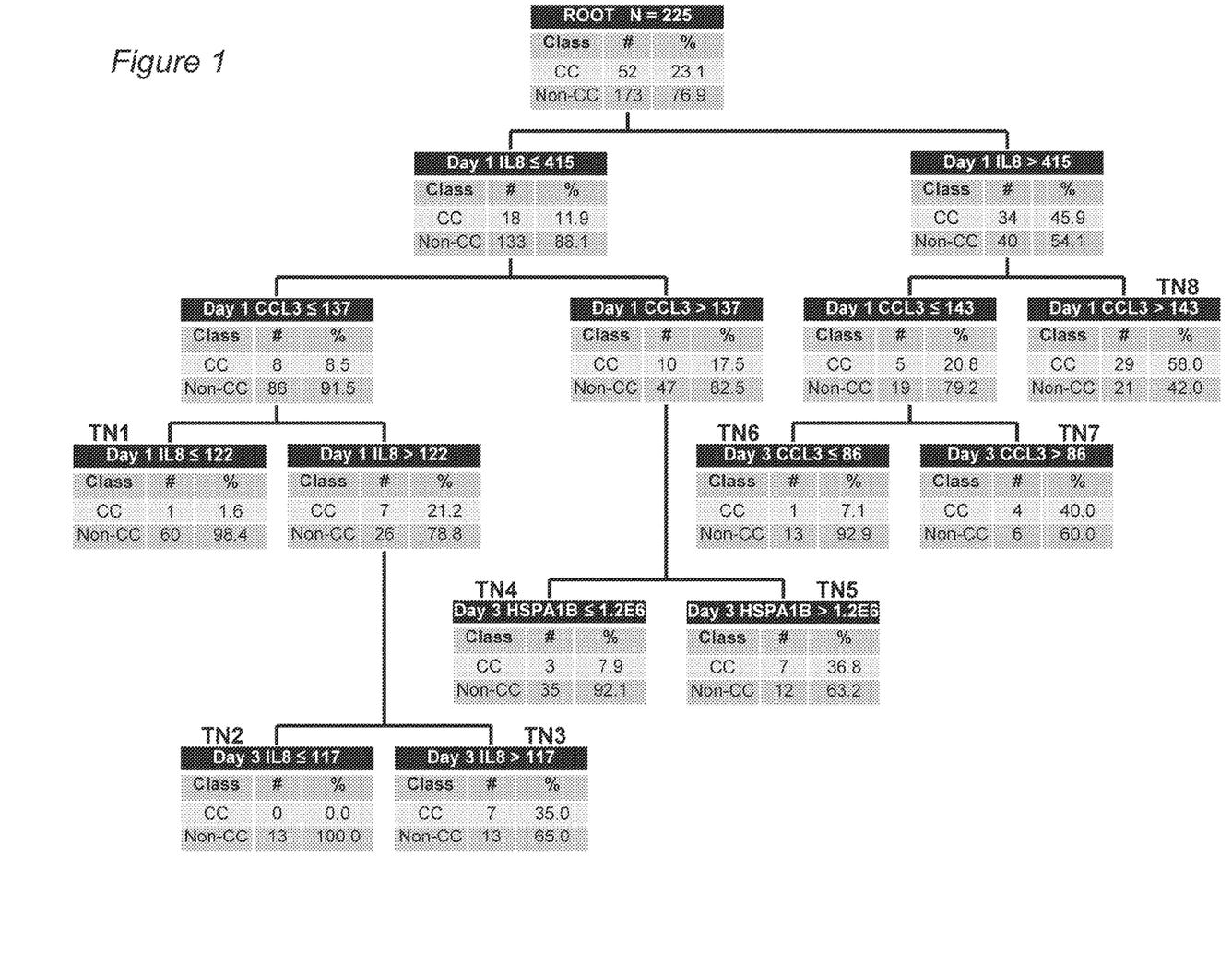

FIG. 1 depicts the derived model. Maximum accuracy was achieved with five biomarker variables, namely absolute day 1 IL8 and CCL3 values and absolute day 3 IL8, CCL3, and HSPA1B values. None of the other biomarker variables or age contributed to predictive accuracy. There were four low probability terminal nodes for a complicated course (0.0 to 7.9% probability; terminal nodes TN1, TN2, TN4, and TN6) and four high probability terminal nodes (35 to 58% probability; TN3, TN5, TN7, and TN8). Among the 126 subjects classified as low probability, 121 (96%) had a non-complicated course, and five (4%) had a complicated course. Among the 99 subjects classified as high probability, 47 (47%) had a complicated course. Table 2 shows the diagnostic test characteristics of the derived decision tree.

The test cohort subjects were classified according to the derived model. Among the 50 subjects classified as low probability for a complicated course, 47 (94%) had a non-complicated course, and three (6%) had a complicated course. Among the 24 subjects classified as high probability, 13 (54%) had a complicated course. Table 2 shows the diagnostic test characteristics of tPERSEVERE in the test cohort.

Example 8

Updating tPERSEVERE tPERSEVERE was updated using all 299 subjects in the combined derivation and test cohorts. All potential bio-

TABLE 2

Test characteristics of the decision tree.

|  | Derivation Cohort | Test Cohort | Updated Model |
| --- | --- | --- | --- |
| Number of Subjects | 225 | 74 | 299 |
| Number of True Positives | 47 | 13 | 62 |
| Number of True Negatives | 121 | 47 | 162 |
| Number of False Positives | 52 | 11 | 69 |
| Number of False Negatives | 5 | 3 | 6 |
| Sensitivity | 90% (78-96) | 81% (54-95) | 91% (81-96) |
| Specificity | 70% (62-77) | 81% (68-90) | 70% (64-76) |
| Positive Predictive Value | 47% (37-58) | 54% (33-74) | 47% (39-56) |
| Negative Predictive Value | 96% (91-99) | 94% (82-98) | 96% (92-99) |
| +Likelihood Ratio | 3.0 (2.4-3.8) | 4.3 (2.4-7.7) | 3.1% (2.5-3.8) |
| −Likelihood Ratio | 0.1 (0.1-0.3) | 0.2 (0.1-0.6) | 0.1 (0.1-0.3) |
| Area Under the Curve | 0.85 (0.79-0.90) | 0.83 (0.74-0.93) | 0.84 (0.79-0.89) |

Example 7

Testing tPERSEVERE

Figure 2:
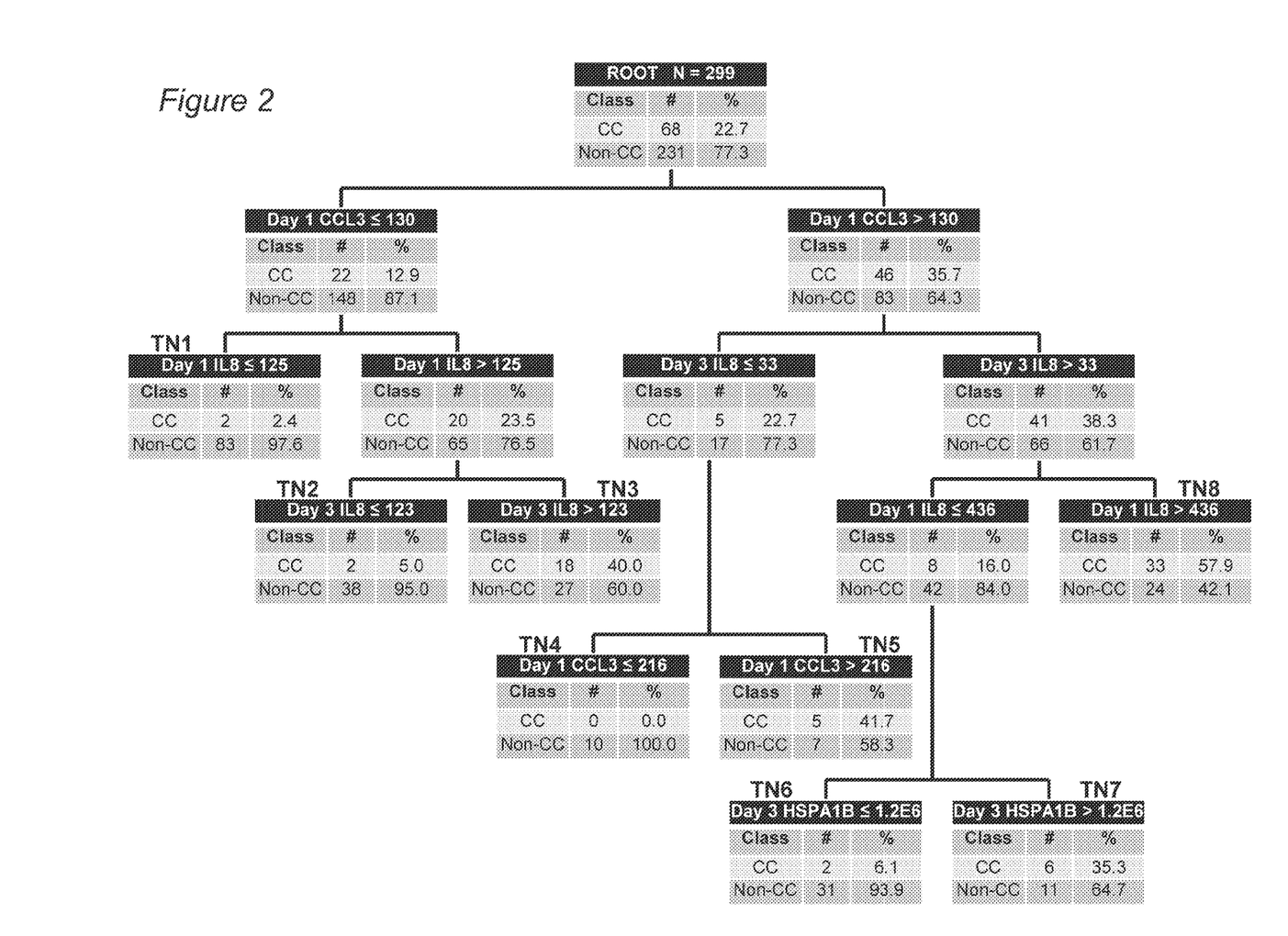

The independent test cohort consisted of 74 subjects with septic shock, of whom 16 (22%) had a complicated course. Table 1 shows the demographics and clinical characteristics of the test cohort. Compared to the derivation cohort, the test cohort subjects had a higher median age, a higher proportion had no race reported, a higher proportion had no causative organism isolated, and a lower proportion had malignancy, immune suppression, or any other co-morbidity. Within the test cohort, the subjects with a complicated course had a lower proportion of males, compared to the subjects with a non-complicated course. No other differences were observed.

marker variables and age were considered in the updating process. FIG. 2 depicts the updated version of tPERSEVERE. Maximum accuracy was achieved with the same biomarker variables as the originally derived decision tree, except that day 3 CCL3 data no longer added to the predictive accuracy. In addition, a day 1 CCL3-based decision rule replaced the day 1 IL8-based, first-level decision rule in the originally derived decision tree.

The updated version of tPERSEVERE contains four low probability terminal nodes for a complicated course (0.0 to 6.1% probability; TN1, TN2, TN4, and TN6) and four high probability terminal nodes (35.3 to 57.9% probability; TN3, TN5, TN7, and TN8). Among the 168 subjects classified as low probability, 162 (96%) had a non-complicated course, and six (4%) had a complicated course. Among the 131 subjects classified as high probability, 62 (47%) had a complicated course. Table 2 shows the diagnostic test characteristics of the updated version of tPERSEVERE.

Example 9

Using tPERSEVERE to Monitor Therapeutic Efficacy tPERSEVERE is used to monitor the therapeutic efficacy of a treatment being administered to a patient with septic shock. First, a pediatric patient with septic shock is identified. A first sample from the patient at a first time point and analyzed to determine a first level of at least one biomarker associated with septic shock in pediatric patients in order to determine whether the level is elevated above a cut-off level, wherein the presence of an elevated level indicates that the patient has an elevated likelihood of being classified as high risk for a poor outcome and the absence of an elevated level indicates that the patient has a reduced likelihood of being classified as high risk for a poor outcome. Then, a second sample is obtained from the patient at a second time point, wherein the second time point occurs after a treatment has been administered to the patient. The second sample is then analyzed to determine a second level of the at least one biomarker in order to determine whether the second level is elevated above a cut-off level, wherein the presence of an elevated level indicates that the patient has an elevated likelihood of being classified as high risk for a poor outcome and the absence of an elevated level indicates that the patient has a reduced likelihood of being classified as high risk for a poor outcome. The patient's risk for a poor outcome at each of the time points is then compared in order to determine if the patient's risk for a poor outcome increased or decreased between the time points, where an increased risk for a poor outcome indicates that a therapy has had a poor efficacy, and a reduced risk for a poor outcome indicates that a therapy has had a good efficacy.

Example 10

Using tPERSEVERE to Provide Individualized Treatment tPERSEVERE is used to provide individualized treatment for a pediatric patient with septic shock. First, the therapeutic efficacy of a treatment being administered to a pediatric patient with septic shock is determined as described in Example 9. If a treatment is determined to have had a poor efficacy, that treatment is discontinued, thereby providing individualized treatment.

Example 9

Using tPERSEVERE to Improve Outcome tPERSEVERE is used to improve an outcome for a pediatric patient with septic shock. First, the therapeutic efficacy of a treatment being administered to a pediatric patient with septic shock is determined as described in Example 9. If a treatment is determined to have had a poor efficacy, that treatment is discontinued. The discontinued treatment which has had a poor efficacy is then replaced with a different treatment, in order to achieve an improved outcome. The alternative treatment can be a high risk therapy.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method of monitoring the therapeutic efficacy of a first treatment administered to a patient with septic shock, and administering to the patient a second treatment, the method comprising:
    analyzing a first sample that has been obtained from the patient at a first time point, which is during day 1 of presentation with septic shock and before the first treatment has been administered, to determine a first serum concentration level of each of three biomarkers consisting of C-C chemokine ligand 3 (CCL3), interleukin-8 (IL8) and heat shock protein 70 kDa 1B (HSPA1B);
    analyzing a second sample that has been obtained from the patient at a second time point, which is during day 3 of presentation with septic shock and after the first treatment has been administered to the patient, to determine a second serum concentration level of each of the three biomarkers;
    determining whether the level of each biomarker is elevated above a cut-off level at each of the first and second time points,
    identifying the patient as at high risk for a poor outcome where any one of the following is true:
    a) a non-elevated level of CCL3 and an elevated level of IL8 at the first time point, and a highly elevated level of IL8 at the second time point, or
    b) a highly elevated level of CCL3 at the first time point, and a non-elevated level of IL8 at the second time point, or
    c) an elevated level of CCL3 and a highly elevated level of IL8 at the first time point, and an elevated level of IL8 at the second time point, or
    d) an elevated level of CCL3 and a non-highly elevated level of IL8 at the first time point, and elevated levels of IL8 and HSPA1B at the second time point; and
    discontinuing administration of the first treatment and administering to the patient identified as at high risk for a poor outcome a second treatment selected from one or more of extracorporeal membrane oxygenation/life support, plasmapheresis, pulmonary artery catheterization, and high volume continuous hemofiltration.

2. The method of claim 1, further comprising:
    obtaining a third sample from the patient at a third time point, wherein the third time point occurs after a treatment has been administered to the patient;
    analyzing the third sample to determine a third level of the at least one biomarker; and determining whether the third level is elevated above a cut-off level.

3. The method of claim 2, wherein the third time point is 12-36 hours after the second time point.

4. The method of claim 2, further comprising:
    obtaining at least one additional sample(s) from the patient at least one additional time point(s), wherein the at least one additional time point(s) occur after a treatment has been administered to the patient;
    analyzing the at least one additional sample to determine at least one additional level of the at least one biomarker; and
    determining whether the at least one additional level is elevated above a cutoff level.

5. The method of claim 4, wherein the at least one additional time point occurs within the first 60 hours of presentation with septic shock.

6. The method of claim 1, wherein
    a) an elevated level of CCL3 at the first time point corresponds to a serum CCL3 concentration greater than 130 pg/ml,
    b) a highly elevated level of CCL3 at the first time point corresponds to a serum CCL3 concentration greater than 216 pg/ml,
    c) an elevated level of IL8 at the first time point corresponds to a serum IL8 concentration greater than 125 pg/ml,
    d) a highly elevated level of IL8 at the first time point corresponds to a serum IL8 concentration greater than 436 pg/ml,
    e) an elevated level of IL8 at the second time point corresponds to a serum IL8 concentration greater than 33 pg/ml,
    f) a highly elevated level of IL8 at the second time point corresponds to a scrum IL8 concentration greater than 123 pg/ml, and
    g) an elevated level of HSPA1B at the second time point corresponds to a serum HSPA1B concentration greater than 1.20 µg/ml.

7. The method of claim 1, wherein the method further comprises receiving one or more patient demographic data and/or clinical characteristics and/or results from other tests or indicia of septic shock.

8. The method of claim 7, wherein
    a) the patient demographic data comprises the age of the patient, or b) wherein the patient demographic data and/or clinical characteristics and/or results from other tests or indicia of septic shock comprises the septic shock causative organism, the presence or absence of chronic disease, and/or the gender, race, and/or co-morbidities of the patient.

9. The method of claim 1, wherein the determination of whether the level(s) of the one or more biomarkers are elevated is combined with one or more additional population-based risk scores.

10. The method of claim 9, wherein the one or more population-based risk scores comprises pediatric risk of mortality (PRISM) and/or pediatric index of mortality (PIM).

\* \* \* \* \*